United States Patent [19]

Cantrell

[11] Patent Number: 4,613,504

[45] Date of Patent: Sep. 23, 1986

[54] PYRIDINE-SOLUBLE EXTRACTS OF MICROORGANISMS

[75] Inventor: John L. Cantrell, Corvallis, Mont.

[73] Assignee: Ribi ImmunoChem Research, Inc., Hamilton, Mont.

[21] Appl. No.: 670,759

[22] Filed: Nov. 13, 1984

Related U.S. Application Data

[63] Continuation-in-part of Ser. No. 535,039, Sep. 23, 1983, abandoned.

[51] Int. Cl.[4] .................... A61K 35/78; A61K 37/00; A61K 31/705
[52] U.S. Cl. .................... 424/195.1; 514/2; 514/26
[58] Field of Search .................... 424/195.1, 95, 121; 514/2, 26

[56] References Cited

U.S. PATENT DOCUMENTS 3,956,481   5/1976   Jolles et al. .................... 424/92
3,976,544   8/1976   Adam et al. .................... 424/92

OTHER PUBLICATIONS

Meyer et al., J. Natl. Can. Inst., 52: 103–108, 1974.
Ribi et al., Natl. Can. Inst., Monograph, No. 39, 1974.
Pharmacological Basis of Cancer Chemoth., Williams & Wilkins Co., 1975, pp. 245–270.

*Primary Examiner*—Donald B. Moyer
*Assistant Examiner*—John W. Rollins, Jr.
*Attorney, Agent, or Firm*—Burgess, Ryan & Wayne

[57] ABSTRACT

A purified pyridine-soluble extract of a microorganism is disclosed. The extract in a pharmaceutically acceptable medium is useful as an anti-animal tumor agent in the treatment of animals.

10 Claims, 1 Drawing Figure

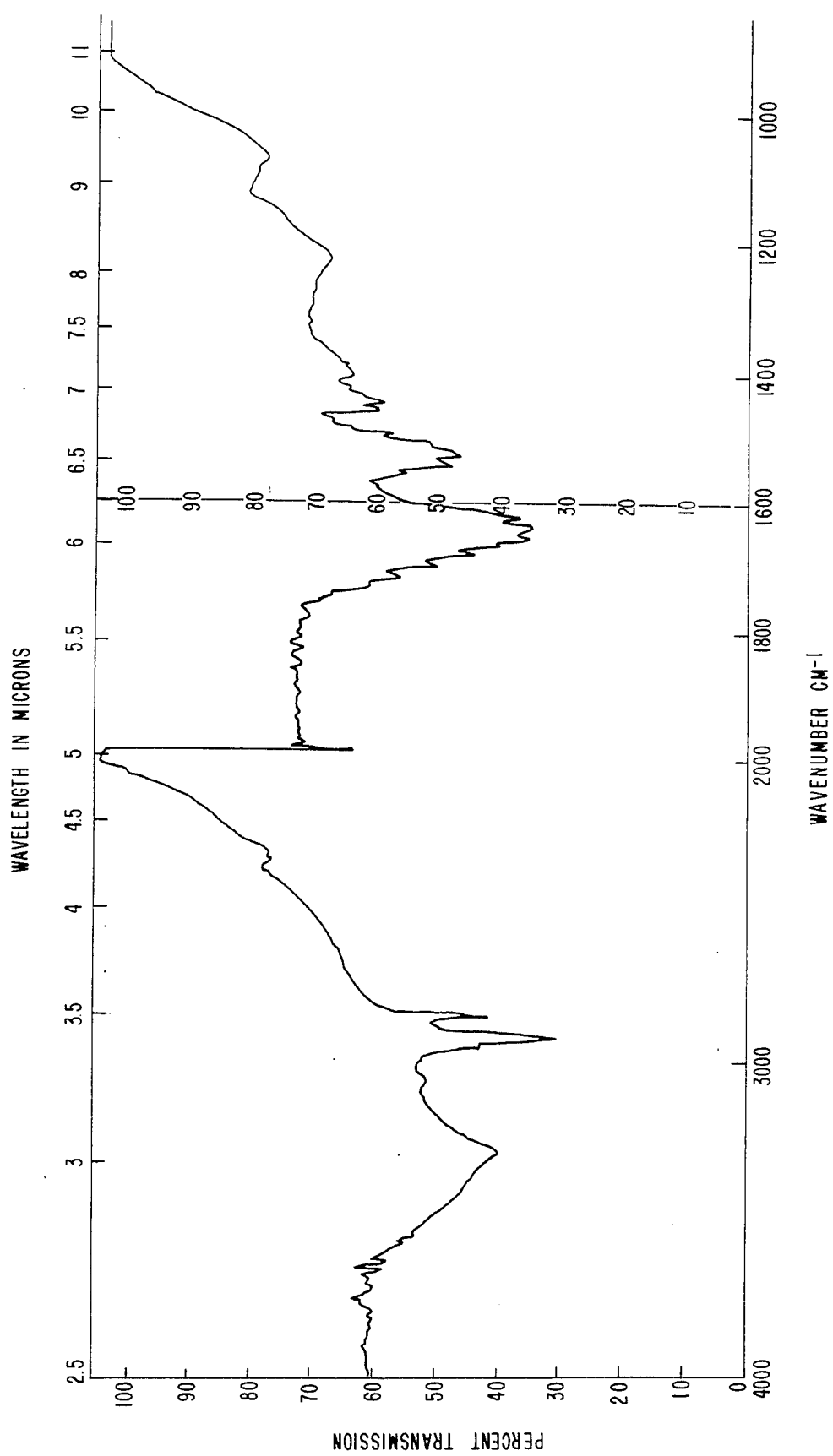

PYRIDINE-SOLUBLE EXTRACTS OF MICROORGANISMS

CROSS-REFERENCE TO RELATED APPLICATION

This application is a continuation-in-part of copending application Ser. No. 535,039 filed Sept. 23, 1983, now abandoned which is embodied herein in its entirety by reference.

BACKGROUND OF THE INVENTION

The present invention is directed to a pyridine-soluble extract of a microorganism which provides a pharmaceutical composition possessing anti-animal tumor properties.

Bacteria such as *Corynebacterium parvum* have been the subject of experimental work to isolate and characterize the component responsible for inducing inhibition of tumor growth [see for example, *Anti Tumor Activity and Lymphoreticular Stimulation Properties of Fractions Isolated from C. parvum;* Cantrell, et al, Cancer Research 39, pgs. 3554–3563 (September, 1979)]. Apart from anti-tumor activity, *C. parvum* is a potent stimulator of the lymphoreticular system resulting in undesirable increases in spleen and liver weights and blastogenesis. It has been discovered that a pyridine-soluble extract of microorganisms possesses potent anti-animal tumor properties without the undesirable toxic effects associated with the prior art products.

It is therefore, an object of the present invention to provide a pharmaceutical composition containing a pyridine-soluble extract of a microorganism.

It is another object of the invention to provide a method of producing the pyridine-soluble extract of a microorganism.

It is still another object of the invention to provide a method of treating tumors in warm blooded animals using the composition containing the pyridine-soluble extract of a microogranism.

A further object of the invention is to provide an aqueous soluble extract derived from the pyridine soluble extract which will facilitate the parenteral injection of an anti-animal tumor active composition.

SUMMARY OF THE INVENTION

The present invention relates to pharmaceutical compositions comprising a pyridine-soluble extract of a microorganism, containing between about 3 and 20% by weight of protein and about 10 to 40% by weight of sugar, and about 35 to 60% by weight of fatty acids. The extract preferably contains about 5% by weight of protein, about 35% by weight of sugar and about 55% by weight of fatty acids.

As used herein, there is no limitation with respect to the use of a sugar; all sugars can be used. The same holds true with respect to fatty acids; there is no limitation with respect to the fatty acids which can be used.

The protein comprises amino acids and ammonia and the amino acids include, for example, the following:

| | |
|---|---|
| Asparginine | 0.273 |
| Threonine | 0.108 |
| Serine | 0.585 |
| Muramic acid | 0.219 |
| Glutamic acid | 0.267 |
| Glycine | 0.39 |
| Alanine | 0.173 |

-continued

| | |
|---|---|
| Diamino pimelic acid | 0.444 |
| Isoleucine | 0.121 |
| Leucine | 0.167 |
| Phenylalanine | 0.034 |
| Histadine | 0.088 |
| Lysine | 0.544 and |
| Ammonia | 0.524 |

The amounts expressed above are in terms of weight percent and the total protein is 6.34% by weight.

The pyridine soluble extract prepared in accordance with the teachings of this invention has been found to have the following elemental analysis:

| Element | Weight Percent |
|---|---|
| Carbon | 60.35 |
| Hydrogen | 9.47 |
| Oxygen | 23.91 |

Additionally, the extract is characterized by an infrared spectrum as indicated in the attached Figure. From the infrared spectrum, the important peaks useful in identifying the extract are set forth in Table 1 below:

| Peak Frequency* ($cm^{-1}$) | Identification |
|---|---|
| 3400 (b) | NH Stretch |
| 3200–2500 (b) | Intramolecular hydrogen bonded OH peak |
| 2920 (s) | CH Stretch |
| 1710 (s) | Ester carbonyl Stretch |
| 1675 (s) | Amide carbonyl Stretch (Amide I Band) |
| 1541 (m) | Amide II Band |

*(b) = broad
(s) = strong
(m) = moderate

Any microorganism may be used to obtain the pyridine-soluble extract including, for example, *M. bovis* BCG, *M. phlei, M. smegmatis, M. kansasii, Nocardia rubra, Nocardia asteroides, Proprionibacterium acnes* Type II, and *Corynebacterium parvum. Corynebacterium parvum* and *Proprionibacterium acnes* Type II are especially preferred.

Whole cells of the microorganism, preferably in the form of a paste, are mixed with pyridine. The resulting mixture is separated to obtain a supernatant fraction which contains the pyridine-soluble extract and a pyridine residue. Optionally, the pyridine residue may be subjected to repeated separation procedures as described above using pyridine to remove further quantities of the desired extract.

The pyridine is then removed from the extract and the dried extract is dialyzed against a suitable liquid such as distilled water. The absence of whole cells or cell fragment contaminants is confirmed by electron microscopy. The resulting purified extract may then be lyophilized by known methods to obtain a stable product.

If the pyridine soluble extract is suspended in water, the suspension can be separated into an aqueous soluble and an aqueous insoluble fraction. The aqueous soluble extract is most desirable since it can be easily injected parenterally while at the same time retaining the anti-animal tumor activity of the pyridine extract.

Both the pyridine-soluble extract and the aqueous soluble extract derived from it, produced in accordance with this invention, have potent anti-tumor activity without stimulating the induction of spleen and liver enlargements. The tumors which may be treated by the instant compositions include animal tumors such as bovine squamous cell carcinoma, bovine fibrosarcoma, equine sarcoid, equine melanoma, equine squamous cell carcinoma, canine mammary tumors, canine adenoma and canine melanoma.

The composition is suitably administered parenterally in a pharmaceutically acceptable medium such as saline or an oil-droplet emulsion directly into the tumor under conditions more particularly described below. Administration can also be by intravenous infusions. The aforesaid composition may be stabilized as for example, by a lyophilization procedure and then reconstituted without loss of potency.

DESCRIPTION OF THE PREFERRED EMBODIMENTS

The amount of the pyridine-soluble extract in a single injection for the treatment of animals is between about 300 ug and 2000 ug. In animals, the instant composition is administered at intervals of about two weeks; up to about 6 injections.

The present composition in a suitable injection medium such as saline or an oil-droplet emulsion is administered directly into tumors. The amount of the pyridinesoluble extract in a single injection is between about 300 and 2000 micrograms as discussed above.

As directed above, the instant composition for treatment of warm blooded animals may be used in the form of a physiologic saline or an oil droplet emulsion. The amount of oil used is in the range of between about 0.5 and 3.0 percent by volume based on the total volume of the composition. It is preferred to use between about 0.75 and 1.5 percent by volume of the oil. Examples of such oils include light mineral oil, squalane, squalene, 7-n-hexyloctadecane, Conoco superoil and Drakeol 6 VR mineral oil (produced by the Penreco Company, Butler, Pa.). The oil is added to the dry pyridine-soluble extract and the mixture is homogenized.

The homogenized oil containing mixture is then combined with a detergent which may optionally be dissolved in a saline solution prior to mixing. The amount of detergent is typically between about 0.02 and 0.25 percent by volume and preferably between about 0.10 and 0.20 percent by volume based on the total volume of the composition. Any common detergent material may be used including Tween-80 and Arlacel (produced by the Atlas Chemical Company).

The mixture resulting from the addition of detergent is then homogenized to form a suspension which has a high percentage of oil droplets coated with the active components as determined by observation under a microscope.

The following examples are for illustrative purposes only and are not intended to limit or in any way redefine the invention as claimed in the claims appended hereto.

EXAMPLE 1

Preparation of Pyridine-Soluble Extract from *Proprionibacterium acnes* Type II

*Proprionibacterium acnes* (P. acnes, Type II (Strain VPI 0204) was grown and harvested at 37° C. in NIH thioglycolate broth for between 48 and 72 hours to obtain a whole cell paste. The paste was then washed with 500 ml of distilled water. 90 grams (wet weight) of the washed paste was mixed with 200 ml. of neat pyridine and centrifuged at $1700\times g$ for one hour at 4° C. A pyridine-soluble extract was removed as a supernatant fraction. The remaining residue was extracted with additional pyridine under identical conditions as described above. Following filtration, using Whatman No. 1 Paper, the pyridine extracts were pooled and the solvent was removed by evaporation at 50° C. in a Buchi Rotavapor (Brinkmann Instruments, Westbury, N.Y.). The dried pyridine extract was extensively dialyzed against distilled water and then lyophilized. The resulting purified pyridine extract contained about 5% by weight of protein, about 35% by weight of sugar and about 55% by weight of fatty acids. The extract was examined under an electron microscope and found to be free of contaminating whole cells and cell wall fragments. The yield of the pyrindine soluble extract was 9% (8.1 g.).

EXAMPLE 2

Preparation of Pyridine-Soluble Extract from *M. bovis* Strain BCG

*M. bovis* strain BCG was grown and harvested in Sautons medium at 37° C. for between 3-4 weeks to obtain a washed whole cell paste. 50 grams (wet weight) of the washed paste was then treated in the same manner as Example 1 to produce a yield of the pyridine-soluble extract of 7% (3.5 g). The extract contained 15% by weight of protein, 10% by weight of sugar and 52% by weight of fatty acids.

EXAMPLE 3

Preparation of Aqueous Extract 500 mg of pyridine extract was sonicated in 100 ml. of distilled water for 15-30 minutes. The resulting suspension was centrifuged at 12,000 rpm in an RC2B centrifuge at 4° C. for 40 minutes. The supernatant was decanted and saved. The residue was extracted two more times, as above. The supernatants were combined in a lyophilizing bottle, shell frozen and lyophilized. Yield 230 mg (46%).

EXAMPLE 4

Mouse ovarian teratocarcinoma

Thirty nine 8-10 week old female C3HEJ mice were injected intraperitoneally with $10^5$ ovarian teratocarcinoma cells. After 24 hours, the mice were injected once with between 0.2 and 0.5 mls of a saline solution containing 1400 ug of each of the active fractions being prepared in accordance with the procedures in Examples 1, 2 and 3. The animals were observed for four weeks.

In a control experiment, fifteen 8-10 week old female C3HEJ mice were injected with $10^5$ ovarian teratocarcinoma. After 24 hours, the mice were injected once with between 0.2 and 0.5 mls of saline. The injections were made intraperitoneally thereby bringing the active material into direct contact with the tumor tissue.

The four groups of mice are compared in the following table:

| Material Injected | Dose per Animal (ug) | No. of Animals | Alive/Total (after 30 days) |
|---|---|---|---|
| *C. parvum* | 1400 | 15 | 5/15 |

-continued

| Material Injected | Dose per Animal (ug) | No. of Animals | Alive/Total (after 30 days) |
|---|---|---|---|
| *P. acnes Type II | 1400 | 15 | 10/15 |
| P. acnes Type II water-soluble fraction | 1400 | 9 | 5/9 |
| Saline | | 15 | 1/15 |

*Pyridine extract

What is claimed is:

1. A pyridine-soluble extract obtained from a microorganism and containing between about 3 and 20% by weight of protein, about 10 to 40% by weight sugar, and about 35 to 60% by weight fatty acids, said extract having the following approximate elemental analysis in weight percent:

| | |
|---|---|
| carbon | 60.35 |
| hydrogen | 9.47 |
| oxygen | 23.91 | and an infrared spectrum as set forth below:

| Peak Frequency (cm$^{-1}$) | Identification |
|---|---|
| 3400 (broad) | NH Stretch |
| 3200–2500 (broad) | Intramolecular hydrogen bonded OH peak |
| 2920 (strong) | CH Stretch |
| 1710 (strong) | Ester carbonyl Stretch |
| 1675 (strong) | Amide carbonyl Stretch (Amide I Band) |
| 1541 (moderate) | Amide II Band |

2. An extract according to claim 1 which is an aqueous soluble extract of the pyridine extract.

3. A pharmaceutical composition comprising an anti-animal tumor effective amount of the extract of claim 1, in combination with a pharmaceutically acceptable carrier.

4. The composition of claim 3 in lyophilized form.

5. The composition of claim 3, wherein said carrier is a saline suspension or an oil droplet emulsion.

6. The composition of claim 5, wherein said oil is present in an amount between about 0.5 and about 3.0% by volume based on the total volume of the composition.

7. The composition of claim 6, further comprising a detergent in an amount between about 0.02 and 0.25% by volume based on the total volume of the composition.

8. The composition of claim 7, wherein the amount of said pyridine-soluble extract is between about 300 and 2,000 micrograms.

9. A method of treating tumors in warm blooded animals, said tumors being selected from the group consisting of bovine squamous cell carcinoma, bovine fibrosarcoma, equine sarcoid, equine melanoma, equine squamous cell carcinoma, canine mammary tumors, canine adenoma and canine melanoma, which comprises administering to said animal an anti-tumor effective amount of the composition of claim 3.

10. The method of claim 9 wherein the amount of said pyridine-soluble extract is between about 300 and 2,000 micrograms.

* * * * *